United States Patent [19]

Djedaini-Pilard et al.

[11] Patent Number: 5,760,016
[45] Date of Patent: Jun. 2, 1998

[54] USE OF MONO-3,6-ANHYDROCYCLODEXTRINS FOR SOLUBILIZING A HYDROPHOBIC COMPOUND AND FOR CONTROLLING THE PURITY OF AN ENANTIOMER AND PROCESS FOR THE PREPARATION OF THESE CYCLODEXTRINS

[75] Inventors: Florence Djedaini-Pilard, Etampes; Bruno Perly, La Verriere, both of France

[73] Assignee: Commissariat a l'Energie Atomique, Paris, France

[21] Appl. No.: 652,467

[22] PCT Filed: Dec. 21, 1994

[86] PCT No.: PCT/FR94/01502

§ 371 Date: Dec. 9, 1996

§ 102(e) Date: Dec. 9, 1996

[87] PCT Pub. No.: WO95/17433

PCT Pub. Date: Jun. 29, 1995

[30] Foreign Application Priority Data

Dec. 22, 1993 [FR] France ................... 93 15470

[51] Int. Cl.$^6$ ............... A61K 31/70; C08B 31/16
[52] U.S. Cl. ....................... 514/58; 536/103
[58] Field of Search ............... 514/58; 536/55.1, 536/103

[56] References Cited

U.S. PATENT DOCUMENTS 4,983,586  1/1991  Bodor ....................... 514/58

OTHER PUBLICATIONS

Gadelle et al, Angew. Chem. Int. Ed. Engl. 30 (1991, No. 1 pp. 78–80.
Fujita et al, Chemistry Letters, pp. 593–596, 1988.
Ashton et al, Angewandte Chemie, International Edition, vol. 30, No. 1, 1991, pp. 80–81.
Ashton et al, Journal of Organic Chemistry, vol. 56, 1991, pp. 7279–7280.

*Primary Examiner*—Elli Peselev
*Attorney, Agent, or Firm*—Oblon, Spivak, McClelland, Maier & Neustadt, P.C.

[57] ABSTRACT

The invention relates to the use of mono-3,6-anhydrocyclodextrins for solubilizing a hydrophobic compound and for controlling the purity of an enantiomer.

The mono-3,6-anhydrocyclodextrin complies with the following formula:

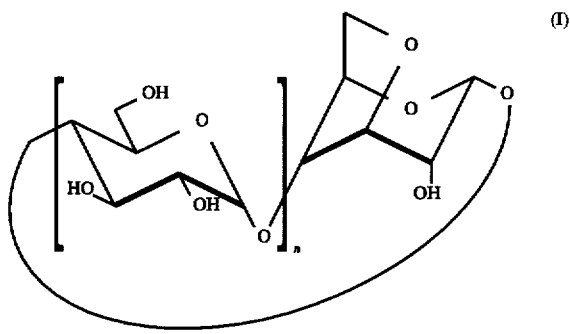

in which n is equal to 5, 6 or 7. Preferably n is equal to 6. The hydrophobic compound can be a steroid such as prednisolone.

17 Claims, 1 Drawing Sheet

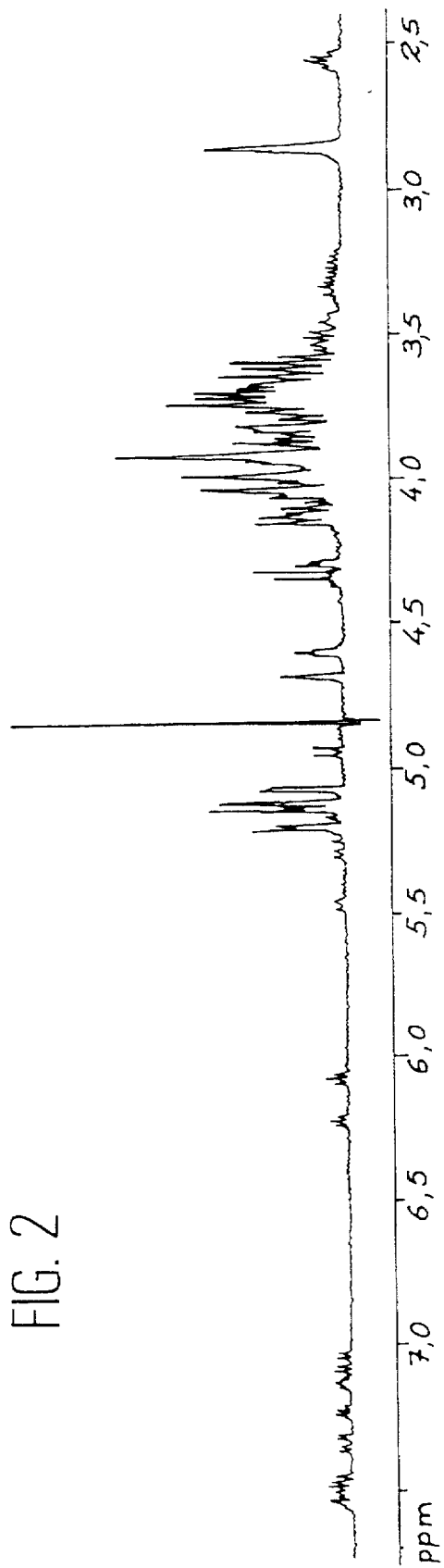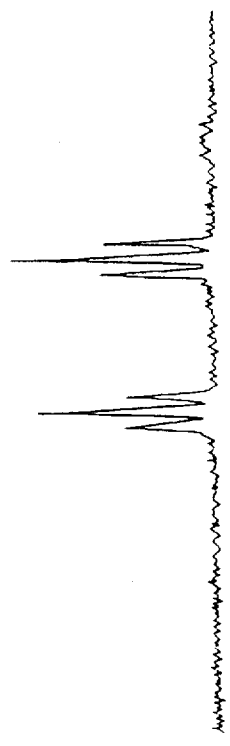

USE OF MONO-3,6-ANHYDROCYCLODEXTRINS FOR SOLUBILIZING A HYDROPHOBIC COMPOUND AND FOR CONTROLLING THE PURITY OF AN ENANTIOMER AND PROCESS FOR THE PREPARATION OF THESE CYCLODEXTRINS

The present invention relates to the use of derivatives of cyclodextrins for solubilizing in an aqueous medium hydrophobic chemical compounds, in particular pharmaceutically active molecules, by the inclusion of these molecules in the cyclodextrin derivative.

Cyclodextrins or cyclomaltooligosaccharides are compounds having a natural origin forming by a linking of 6, 7 or 8 glucose units bonded in χ-1,4. Numerous works have shown that these cyclodextrins could form inclusion complexes with hydrophobic molecules and thus permit the solubilization of these molecules in aqueous media. Numerous applications have been proposed for taking advantage of this phenomenon, particularly in the pharmaceutical field, as is described by D. Duchêne in the work entitled "Cyclodextrins and their industrial uses", chapter 6, pp 213 to 257, Editions de Santé, 1987. Pharmaceutical compositions using these cyclodextrins have also been marketed in Japan and Italy and more recently in France, e.g. by Pierre Fabre Medicament for Brexin$^{(R)}$, which is an inclusion complex of Piroxicam in β-cyclodextrin.

Among the usable cyclodextrins, β-cyclodextrin, which has 7 glucose units, is the most appropriate with regards to the size of its cavity and is the least expensive of the three, but its use causes certain problems, because it is less soluble than other cyclodextrins and has a hemolytic character.

Consideration has also been given to the improvement of the properties of β-cyclodextrin by chemically modifying to make it more suitable. Several solutions have been envisaged and have led to the use of methyl derivatives or hydroxyalkyl derivatives.

Methyl derivatives are much more soluble than the original cyclodextrin and they have good properties of solubilizing hydrophobic, organic compounds, particularly in the case of 2,6-dimethyl-β-cyclodextrin. However, these methyl derivatives, apart from the fact that they are difficult to obtain in the pure state, are unusable for pharmaceutical applications, particularly for injectable forms, due to their very pronounced hemolytic character.

The hydroxyalkyl derivatives more particularly developed by Janssen, e.g. hydroxypropyl-cyclodextrins have a very high solubility in water and are only slightly hemolytic. However, their use remains difficult due to their extreme chemical heterogeneity. In addition, substitutions can limit the formation of inclusion complexes by steric hindrance and as yet no pharmaceutical application has been developed with these derivatives.

The present invention specifically relates to the use of other derivatives of cyclodextrins for the solubilization of hydrophobic chemical compounds making it possible to obviate these disadvantages. It also relates to a novel process for the preparation of the cyclodextrin derivatives leading to very pure products without requiring laborious purification stages.

According to the invention, the process for solubilizing a hydrophobic chemical compound in an aqueous medium consists of combining the hydrophobic chemical compound with a mono-3,6-anhydrocyclodextrin of formula:

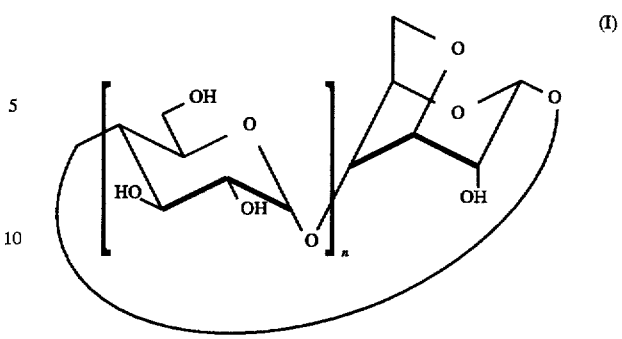

in which n is equal to 5, 6 or 7, to for therewith a water-soluble inclusion complex.

The use in this process of the monoanhydrocyclodextrin derivative complying with the aforementioned formula has the advantage of improving the solubility, stability and bioavailability, in various administration forms of the hydrophobic compound, particularly in the case of pharmaceutically active molecules.

In particular, the solubility in water of these derivatives is considerable and greatly superior to that of the parent cyclodextrin, particularly with respect to β-cyclodextrin. Moreover, these cyclodextrin derivatives have a much weaker hemolytic character than the parent cyclodextrin. These cyclodextrin derivatives also have the property of different affinities for the isomers of a mixture of isomers and can be consequently used in chromatography-based isomer separation processes. They also make it possible to easily carry out a purity control of the enantiomer, because the inclusion complexes formed with racemic chiral compounds have in nuclear magnetic resonance spectrometry an easily observable separation of the characteristic signals of each enantiomer.

According to the invention, preference is given to the use of the monoanhydro derivative of β-cyclodextrin, i.e. the derivative of formula (I) with n=6. However, it is also possible to use the derivatives of χ-cyclodextrin (n=5) or γ-cyclodextrin (n=7).

The hydrophobic chemical compounds which can be solubilized in aqueous media by means of these cyclodextrins can be of different types.

As examples of such compounds, reference can be made to cosmetic products, vitamins, pharmaceutically active molecules like those described by D. Duchêne in the work entitled "Cyclodextrins and their industrial uses", chapter 6, pp 213–257, Editions de Santé, 1987.

Preferably, in the present invention, the hydrophobic chemical compound is a pharmaceutically active molecule.

As examples of such molecules, reference can be made to steroids, e.g. prednisolone, anit-epileptic agents such as carbamazepine, and anti-cancer agents.

The cyclodextrin derivatives of formula (I) used in the invention can be prepared by the process described in Chemistry Letters, pp 543–546, 1988, by reacting a corresponding monotosyl derivative with an aqueous soda solution. After this reaction, it is possible to isolate the monoanhydro derivative in the pure state by carrying out advanced high performance liquid chromatography purifications in order to eliminate the byproducts and salts.

In addition, according to the invention, use is preferably made for the preparation of these derivatives of a simpler process making it possible to avoid these purification stages.

The invention also relates to a process for the preparation of a mono-3,6-anhydrocyclodextrin of formula:

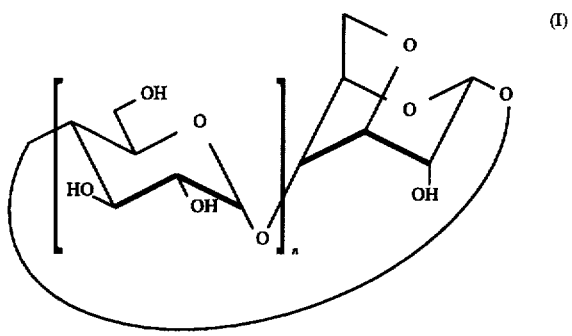

(I)

in which n is equal to 5, 6 or 7 consisting of reacting a monotosyl derivative of cyclodextrin of formula:

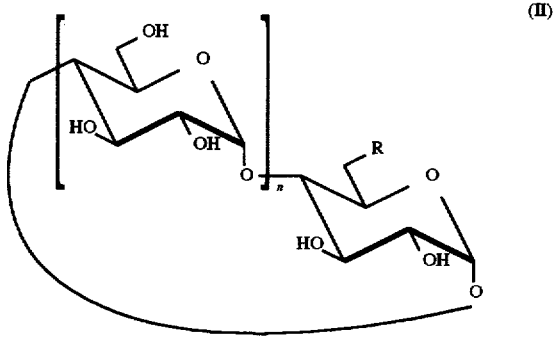

(II)

in which R is the tosyl group and n is equal to 5, 6 or 7, with lithia in an aqueous medium.

The use of lithia in place of soda makes it possible to much more easily obtain the monoanhydrocyclodextrin derivative and to then carry out its separation from the reaction medium under better conditions.

This separation can be carried out by precipitation after the acidification of the reaction medium and by repeating these precipitation stages, it is possible to isolate the cyclodextrin derivative in the pure state without it being necessary to carry out complimentary, chromatography-based purification stages.

Precipitation can be carried out by adding the aqueous medium after acidification to an organic solvent, such as acetone, and then separating the precipitate formed by centrifuging. This makes it possible to eliminate all the sulphonic acid derivatives soluble in the organic solvent, as well as the salts, because lithium chloride is soluble in an organic solvent such as acetone.

The invention also relates to the inclusion complexes of a mono-3,6-anhydrocyclodextrin complying with formula (I) with a hydrophobic chemical compound, particularly a pharmaceutically active molecule.

This inclusion complex can be prepared by conventional processes, e.g. by adding to a solution or suspension of the mono-3,6-anhydrocyclodextrin used, a solution of the hydrophobic compound in an appropriate organic solvent, e.g. acetone. It is then possible to isolate the inclusion complex formed by lyophilization.

These inclusion complexes, when they are formed with pharmaceutically active molecules, can in particular be used in pharmaceutical compositions, which also include the pharmaceutically acceptable vehicle.

These pharmaceutical compositions, which can be administered orally or parenterally, are e.g. solutions, powders, suspensions, etc. and in particular injectable solutions.

As stated hereinbefore, the inclusion complexes formed with the mono-3,6-anhydrocyclodextrins of formula (I), and racemic, chiral compounds have the interesting property, in nuclear magnetic resonance, of separate signals for each enantiomer.

The invention also relates to a process for controlling the purity of an enantiomer of an organic compound, which consists of combining this enantiomer with a mono-3,6-anhydrocyclodextrin according to formula (I) for forming an inclusion complex of said enantiomer and subjecting the complex obtained to nuclear magnetic resonance spectrometry for detecting the possible presence of the other enantiomer on the spectrum obtained.

The invention also relates to a process for the separation of isomers by chromatography, which consists of circulating a mixture of these isomers in a column filled with a solid chromatographic support, to which is covalently fixed a mono-3,6-anhydrocyclodextrin of formula (I) according to the invention and separately collecting the isomers at the column exit.

The chromatographic support used can be formed by an insoluble polymer or microparticles of silica. The insoluble polymers can in particular be agarose and polysaccharides of the Sephadex$^{(R)}$ types.

The chemical grafting of the cyclodextrins according to the invention to the chromatographic supports can be carried out by means of a coupling reagent such as epichlorohydrin, which ensures the coupling between an OH group of the cyclodextrin and an OH group of the chromatographic support.

The property of the cyclodextrins according to the invention of having a different affinity for each of the isomers makes it possible to obtain a good separation thereof by chromatography. The isomers can be optical isomers, position isomers or diastereoisomers.

Other features and advantages of the invention can be better gathered from the following illustrative and non-limitative examples, with reference to the attached drawings, wherein show:

FIG. 1 The nuclear magnetic resonance spectrum of an inclusion complex of mono-3,6-anhydrocyclomaltoheptaose with a racemic mixture of dothiepin.

FIG. 2 A larger-scale portion of the spectrum of FIG. 1.

EXAMPLE 1

Preparation of mono-3,6-anhydrocyclomaltoheptaose

In order to carry out the synthesis according to the process of the invention, preparation firstly takes place of the mono-6-tosyl-deoxy-cyclomaltoheptaose by the action of p-toluene sulphonyl chloride on β-cyclodextrin in an aqueous medium.

60 g of cyclomaltoheptaose (52.8 mmole) are suspended in 500 ml of distilled water. Dropwise addition takes place of 6.57 g (164 mmole) of caustic soda dissolved in 20 ml of water over 5 minutes and with strong magnetic stirring. To the clear solution obtained are added 10.08 g (52.9 mmole) of p-toluene sulphonyl chloride (tosyl chloride) in 30 ml of acetonitrile in dropwise manner over 10 minutes. After stirring for 2 hours at ambient temperature, the precipitate formed is eliminated by filtration and the filtrate is kept for 48 hours at 4° C. The precipitate is isolated by filtration in vacuo, washed with 50 ml of ice water and recrystallized immediately in boiling water. After one night at 4° C., the precipitate is filtered and dried in vacuo at 30° C. This gives 7.5 g (12%) of a pure compound in accordance with the specifications.

Dissolving then takes place of 100 mg of the previously obtained 6-tosyl-6-deoxy-cyclomaltoheptaose in 10 ml of 1M LiOH in water, dissolving being immediate. The solution is kept at 40° C. for 15 hours and is then acidified to a pH of approximately 3 using 1M HCl. The solution is then added dropwise and accompanied by stirring to 20 ml of pure acetone. A vitreous precipitate is formed, which is isolated by centrifuging (6000 rpm, 10 min) and the precipitate is redissolved in 0.5 ml of water. This precipitation is repeated and the residue again isolated by centrifuging, followed by redissolving in water and lyophilization.

The structure of the product obtained is confirmed by nuclear magnetic resonance of the high field proton and in this way spectral characteristics are obtained in accordance with those given in Chemistry Letters, pp 543-546, 1988.

The solubility in water of the compound obtained is 520 g/l at 25° C., i.e. close to 30 times that of the original cyclodextrin, which is 18 g/l. This solubility is also at least twice that of $\chi$ and $\gamma$-cyclodextrins.

The hemolytic properties of this derivative were tested by contacting 0.4 ml of a suspension of human erythrocytes and a 5 mmole/l solution of this derivative, at a pH of 7.4, for 30 min at 37° C. Under these conditions, the derivative reveals 0% hemolysis, whereas the hemolysis percentage is 50% for $\beta$-cyclodextrin under the same conditions.

Other tests revealed the absence of hemolytic properties at much higher concentrations (no hemolysis detectable at 50 mmole/l).

EXAMPLE 2

Preparation of an inclusion complex of mono-3,6-anhydrocyclo-maltoheptaose and prednisolone The prednisolone is in accordance with the following formula:

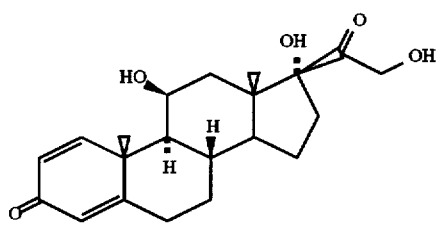

and has a very low solubility in water (0.25 mg/ml at 25° C., i.e. 0.7 mole/l). 10 µmole of mono-3,6-anhydrocyclomaltoheptaose prepared in example 1 are dissolved in 1 ml of pure water (apyrogenic water for injections) and addition takes place of 5 µmole of prednisolone in the form of a 50 mmole/l concentrated solution in acetone. The acetone is eliminated under nitrogen bubbling and the solution lyophilized.

The residual solid, which contains 10 µmole of the cyclodextrin derivative and 5 µmole of prednisolone, is redissolved in the minimum of water at 25° C. This minimum corresponds to 50 µl of water, which indicates a maximum prednisolone solubility in water of 100 mmole/l in the presence of said cyclodextrin derivative at a concentration of 200 mmole/l. Under the same conditions, $\beta$-cyclodextrin only makes it possible to solubilize prednisolone at 9 mmole/l.

Thus, a much better result is obtained with the monoanhydro derivative of said cyclodextrin.

EXAMPLE 3

Preparation of an inclusion complex of mono-3,6-anhydrocyclo-maltoheptaose with dothiepin in the form of the racemic mixture The dothiepin corresponds to the formula:

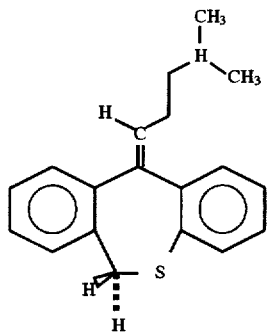

This molecule is optically active by the absence of symmetry with respect to the aromatic plane and the commercial compound is a racemic product. The inclusion complex of this racemic compound is prepared by forming an aqueous solution of dothiepin hydrochloride and mono-3,6-anhydrocyclo-maltoheptaose containing 5 mmole/l of hydrochloride and 10 mmole/l of the cyclodextrin derivative. The solution is then examined by nuclear magnetic resonance spectrometry at 500 MHz and 298K. The spectrum obtained under these conditions is shown in FIGS. 1 and 2.

FIG. 1 shows the complete spectrum, whilst FIG. 2 shows on a larger scale that part of the spectrum of FIG. 1 corresponding to the signals of the two enantiomers.

In FIG. 2, it is possible to see that there is a good separation of the signals of the vinyl protons, which reaches 0.2 ppm, whereas this separation is only 0.03 ppm on using $\beta$-cyclodextrin under the same conditions.

Thus, the cyclodextrin derivatives according to the invention can be used as a chiral reagent for establishing the degree of purity of an enantiomer.

We claim:

1. A process for the preparation of a mono-3,6-anhydrocyclodextrin of formula:

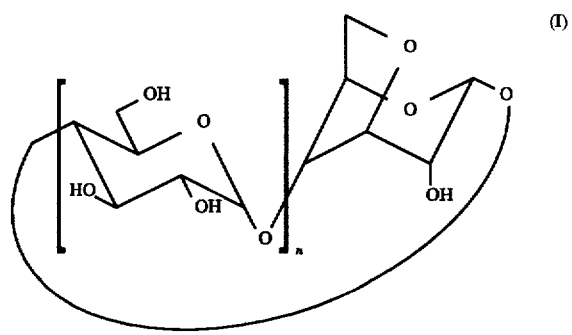

in which n is 5, 6 or 7, comprising reacting a monotosyl cyclodextrin of formula:

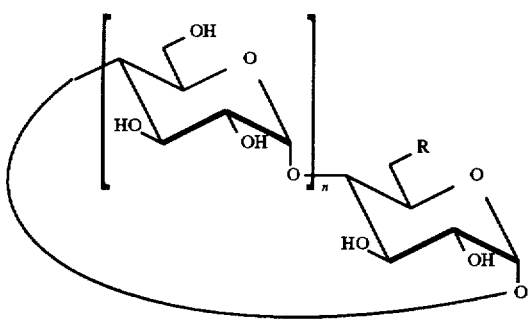

in which R is a tosyl group and n is 5, 6 or 7, with lithia in an aqueous medium.

2. The process according to claim 1, further comprising separating said mono-3,6-anhydrocyclodextrin from said medium by precipitation.

3. The process according to claim 1, wherein n is 6.

4. A process for solubilizing a hydrophobic chemical compound in an aqueous medium, comprising combining the hydrophobic chemical compound with a mono-3,6-anhydrocyclodextrin of formula:

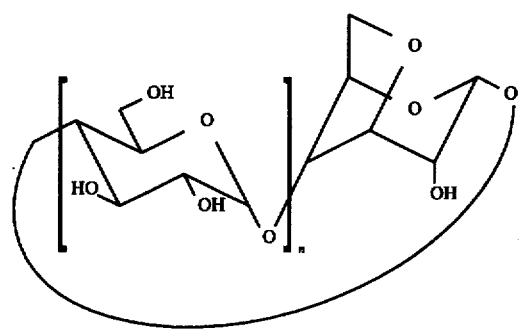

in which n is 5, 6 or 7, to form a water-soluble inclusion complex.

5. An inclusion complex of a mono-3,6-anhydrocyclodextrin of formula:

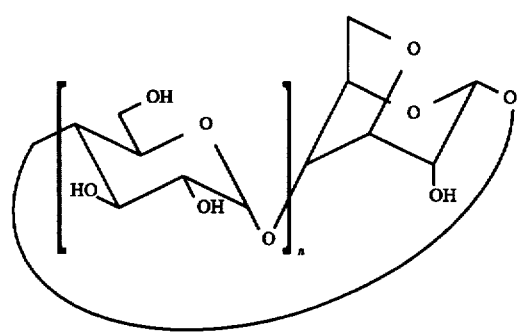

in which n is 5, 6 or 7, with a hydrophobic chemical compound.

6. The complex according to claim 5, wherein n is 5.
7. The complex according to claim 5, wherein n is 6.
8. The complex according to claim 5, wherein n is 7.

9. The complex according to claim 5, wherein the hydrophobic chemical compound is a pharmaceutically active molecule.

10. The complex according to claim 9, wherein said pharmaceutically active molecule is prednisolone.

11. A pharmaceutical composition, comprising the inclusion complex according to claim 5 and a pharmaceutically acceptable vehicle.

12. The pharmaceutical composition according to claim 11, wherein said hydrophobic chemical compound is a pharmaceutically active molecule.

13. A pharmaceutical composition according to claim 12, wherein said pharmaceutically active molecule is prednisolone.

14. A process for controlling the purity of an enantiomer of an organic compound, comprising combining said enantiomer with a mono-3,6-anhydrocyclodextrin of formula:

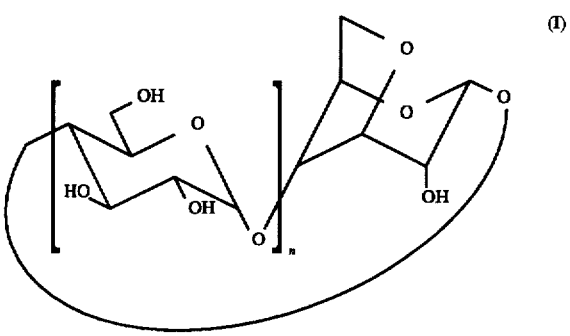

in which n is 5, 6 or 7, to form an inclusion complex of said enantiomer and subjecting said inclusion complex obtained to nuclear magnetic resonance spectrometry for detecting the presence or absence of a different enantiomer.

15. The process according to claim 14, wherein n is 6.

16. The process according to claim 14, wherein said organic compound is dothiepin.

17. A process for the separation of isomers by chromatography, comprising circulating a mixture of isomers in a column filled with a solid chromatographic support to which is covalently fixed a mono-3,6-anhydrocyclodextrin of formula (I):

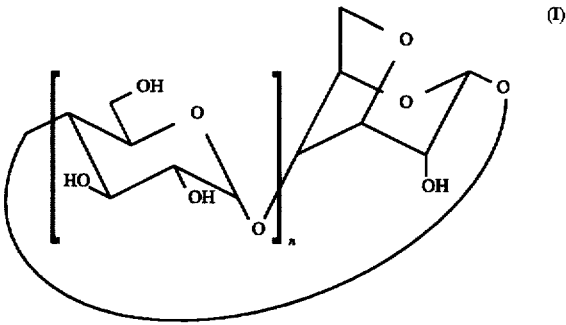

in which n is 5, 6 or 7 and collecting separated isomers from said column.

* * * * *